(12) United States Patent
Gorsek

(10) Patent No.: US 6,572,897 B1
(45) Date of Patent: Jun. 3, 2003

(54) INSULIN SENSITIVITY MAINTENANCE AND BLOOD SUGAR LEVEL MAINTENANCE FORMULATION FOR THE PREVENTION AND TREATMENT OF DIABETES

(75) Inventor: Wayne F. Gorsek, Boynton Beach, FL (US)

(73) Assignee: Vitacost.com, Inc., Boynton Beach, FL (US)

( * ) Notice: Subject to any disclaimer, the term of this patent is extended or adjusted under 35 U.S.C. 154(b) by 0 days.

(21) Appl. No.: 10/187,613

(22) Filed: Jul. 3, 2002

(51) Int. Cl.⁷ .................... A01N 59/16; A61K 33/24
(52) U.S. Cl. ........................................ 424/655
(58) Field of Search ........................ 424/655, 725

(56) References Cited

U.S. PATENT DOCUMENTS

| | | | |
|---|---|---|---|
| 5,730,988 A | * 3/1998 | Womack | 424/646 |
| 5,900,240 A | * 5/1999 | Tomer et al. | 514/866 |
| 5,980,902 A | * 11/1999 | Edayatimangalam et al. | 424/195.1 |
| 6,103,756 A | * 8/2000 | Gorsek | 514/458 |
| 6,440,451 B1 | * 8/2002 | Schumacher | 424/725 |

OTHER PUBLICATIONS

Computer Derwent DWPI 2001–294533 Kenko Tsusho KK Abstract JP 2001048802 Feb. 20, 2001.*
Computer JPAB Abstract JP02000169384 Matsuyama Dec. 9, 1998.*
Computer EPAB Abstract EP001022022 Matusyama Jul. 26, 2000.*

* cited by examiner

Primary Examiner—Herbert J. Lilling
(74) Attorney, Agent, or Firm—Hoffman, Wasson & Gitler PC

(57) ABSTRACT

A composition that contains the most potent combination of nutrients with clinical studies proven to assist in the maintenance of insulin sensitivity and healthy blood sugar levels. The formulation contains essential amounts of Alpha Lipoic Acid, Chromium, Lutein, Bioflavonoids(quercetin and rutin), Mormordica Charantia extract, Corosolic Acid, and Gymnema Sylvestre Extract, as well as other ingredients and healthy filler ingredients.

2 Claims, No Drawings

INSULIN SENSITIVITY MAINTENANCE AND BLOOD SUGAR LEVEL MAINTENANCE FORMULATION FOR THE PREVENTION AND TREATMENT OF DIABETES

BACKGROUND OF THE INVENTION

The invention relates to a composition that contains the most potent combination of nutrients with clinical studies proven to assist in the maintenance of insulin sensitivity and healthy blood sugar levels.

The advanced formulation is designed to promote healthy blood sugar levels as people age which is critical to good health.

High levels of blood sugar are associated with adverse affects on our vision, heart/circulation, kidneys and nervous system. This is commonly associated with the disease of diabetes. Individual vitamins, minerals, herbs and antioxidants have been studied for their efficacy at promoting healthy blood sugar and protecting cells from the damage of elevated blood sugar levels. This prevents heart disease and strokes.

It is an object of the present invention to provide an unique formulation which allows individuals improve, maintain and optimize blood sugar levels, and prevent and reverse diabetes and the complications associated therewith.

SUMMARY OF THE INVENTION

The key to the unique formulation is a combination of specific vitamins, minerals, herbs and nutrients. These essential components in the amounts provided uniquely contribute to improved blood sugar levels and insulin delivery to the cells. The formulation will protect the healthy cells in the body from being damaged by blood glucose. This process is called glycation.

The formulation contains essential amounts of Alpha Lipoic Acid, Chromium, Lutein, Bioflavonoids(quercetin and rutin), Mormordica Charantia extract, Corosolic acid, and Gymnema Sylvestre Extract, as well as other ingredients and healthy filler ingredients. It prevents and reduces the glycosylation of hemoglobin.

Diabetics have a high level of oxidative stress and this formulation reduces the oxidative stress which causes diabetic complications.

The formulation is preferably delivered in capsule form at 8 capsules per day.

DETAILED DESCRIPTION OF THE INVENTION

The present invention involves a composition for oral ingestion that contains Alpha Lipoic Acid, Chromium, Lutein, Bioflavonoids(quercetin and rutin), Mormordica Charantia extract, Corosolic Acid, and Gymnema Sylvestre Extract, as well as other ingredients and healthy filler ingredients. More specifically, this formulated product is a blood sugar level maintenance and management formulation. This formulation allows for enhanced maintenance of insulin and provides required nutrients to combat heart disease, diabetes and strokes.

In order to secure the desired result the following essential components are provided:

Alpha Lipoic Acid is an essential antioxidant which has free radical quenching properties. Alpha Lipoic Acid functions in both fat and water soluble tissues and provides antioxidant protection for healthy nerves and healthy blood sugar levels (600 mg).

The rare mineral chromium plays a major role in the sensitivity of cells to insulin. Supplementing the diet with chromium can decrease fasting blood glucose levels, improve glucose tolerance, lower insulin levels, and promote healthy cholesterol and triglyceride levels (500 mcg) (50 mcg–5,000 mcg).

Lutein is an antioxidant found naturally occurring fat-soluble pigments in plants. Recent studies indicate that Lutein promotes healthy vision as well as a healthy cardiovascular system (6 mg) (0.6–60 mg).

Bioflavonoids including Quercetin (200 mg) (20 mg–2,000 mg) and Rutin (200 mg) (20 mg–2,000 ng) are also essential for the overall maintenance of healthy levels of blood sugar.

Mormordica Charantia Extract (standardized for 2.5% bitter principles, 0.5% Charantin) (500 mg) (50 mg–5,000 mg) is an essential ingredient from bitter melon a tropical fruit widely cultivated in Asia and south America. The blood sugar lowering of the extract has been established in human clinical trials.

Corosolic Acid (lagerstroemia speciosa 1) is an essential component for blood sugar maintenance (48 mg) (4.8 mg–480 mg).

Gymnema Sylvestre (standardized for 25% Gymnemic acids) (600 mg) (60 mg–6,000 mg).

Additionally, the following Vitamins, Minerals and natural supplement additives are all important for the memory health formulation:

|  | Amount per serving | % daily value |
| --- | --- | --- |
| Vitamin A (betatene ®) (as natural carotenoids beta carotene, alpha carotene, lutein, zeaxanthin, cryptoxanthin and palmitate) | 5,000 IU | 100% |
| Vitamin C (Ester C ®) (as magnesium ascorbate) | 1 g (1,000 mg) | 1,666% |
| Vitamin D3 (as cholecalciferol) | 400 IU | 100% |
| Natural Vitamin E (as d-alpha tocopherol succinate, gamma, delta and beta) | 500 IU | 1,666% |
| Thiamine (Vitamin B1 HCL) | 200 mg | 13,333% |
| Riboflavin (Vitamin B2) | 10 mg | 588% |
| Niacin (Vitamin B3) | 100 mg | 500% |
| Pyridoxine HCL (Vitamin B6) | 100 mg | 5,000% |
| Folic Acid (as folacin) | 800 mcg | 200% |
| Vitamin B12 (Methylcobalamin) | 2 mg | 33,332% |
| Biotin | 3 mg | 1,000% |
| Pantothenic Acid (Vitamin B5 as d-calcium pantothenate) | 100 mg | 1,000% |
| Magnesium (as Ascorbate) (Ester C) | 68 mg | 17% |
| Magnesium (as Citrate) | 232 mg | 58% |
| Zinc (as OptiZinc ®) | 15 mg | 100% |
| Selenium (Selenomethionine) | 200 mcg | 285% |
| Copper (as chelate) (AAC) | 1 mg | 50% |
| Manganese (as chelate) (ACC) | 1 mg | 50% |
| Chromium (as chromium polynicotinate) | 400 mcg | 417% |
| Molybdenum (as chelate) (ACC) | 150 mcg | 200% |
| Coenzyme Q10 | 10 mg | ** |
| Alpha Lipoic Acid | 600 mg | ** |
| Black Pepper (Bioperine ®) (piper nigrum) (fruit extract) | 5 mg | ** |

-continued

| | Amount per serving | % daily value |
|---|---|---|
| Milk Thistle Extract | 500 mg | ** |
| Bioflaonoid (Quercetin) | 200 mg | ** |
| Bioflavonoid (Rutin) | 200 mg | ** |
| Green Tea Extract (standardized 98% polyphenols 80% Catechins, 45% EGCG) | 100 mg | ** |
| Plant Enzymes (Amylase 2,000 S KB Cellulase 25 CU, Protease 7,500 HUT, Lipase 25 FIP and Lactase 250 ALU) | 50 mg | ** |
| Inositol | 200 mg | ** |
| Inositol (as Hexaniacinate) | 200 mg | ** |
| Ginkgo Biloba (Ginkoaceace) (leaves) (Standardized 24% ginkgo flavon glycosides, 6% terpene lactones) | 120 mg | ** |
| Lutein Extract (from 120 mg FloraGLO ®) | 6 mg | ** |
| L-Taurine | 100 mg | ** |
| Mormordica Charantia Extract | 500 mg | ** |
| Glucosol | 48 mg | ** |
| Gymnema Sylvestre Extract | 600 mg | ** |
| (other ingredients: Silica, Cellulose, Magnesium Stearate, and Kosher Gelatin (Capsule) | | ** |

In addition to the key components, other components such as kosher gelatin (capsules), magnesium stearate and silica and cellulose are included.

Controlling Blood sugar levels is a confusing and frustrating effort. Only the formulations described help maintain healthy levels for life. Although the invention has been described primarily in connection with special and preferred embodiments, it will be understood that it is capable of modification without departing from the scope of the invention. The following claims are intended to cover all variations, uses, or adaptations of the of the invention, following, in general the principles thereof and including such departures from the present disclosure as come within known or customary practice in the field to which the invention pertains, or as are obvious to persons skilled in the field.

What is claimed is:

1. A healthy blood sugar maintenance composition comprising an effective amount of:

Alpha Lipoic Acid;

Chromium Polynicotinate;

Quercetin;

Rutin;

Lutein;

Mormordical Charantia Extract standardized for 2.5% bitter principles, 0.5% charantin; and Corosolic Acid; and Gymnema Sylvestre Extract.

2. A healthy blood sugar maintenance composition as claimed in claim 1; and comprising an effective amount of approximately:

600 mg Alpha Lipoic Acid;

500 mg Chromium Polynicotinate;

200 mg Quercetin;

200 mg Rutin;

6 mg Lutein;

500 mg Mormordical Charantia Extract;

48 mg Corosolic Acid; and 600 mg Gymnema Sylvestre Extract.

* * * * *